(12) United States Patent
Ko

(10) Patent No.: US 9,358,254 B2
(45) Date of Patent: Jun. 7, 2016

(54) PHARMACEUTICAL USE OF A COMPOSITION INCLUDING A CARBONACEOUS MATERIAL AND AN ACTIVE PARTICLE

(71) Applicant: Feng Chia University, Taichung (TW)

(72) Inventor: Tse-Hao Ko, Taichung (TW)

(73) Assignee: FENG CHIA UNIVERSITY, Taichung (TW)

( * ) Notice: Subject to any disclaimer, the term of this patent is extended or adjusted under 35 U.S.C. 154(b) by 0 days.

(21) Appl. No.: 14/041,666

(22) Filed: Sep. 30, 2013

(65) Prior Publication Data

US 2014/0363483 A1    Dec. 11, 2014

(30) Foreign Application Priority Data

Jun. 5, 2013   (TW) .............................. 102120013 A

(51) Int. Cl.
| | |
|---|---|
| *A61K 33/44* | (2006.01) |
| *A61K 33/38* | (2006.01) |
| *A61K 33/06* | (2006.01) |
| *A61K 33/24* | (2006.01) |
| *A61K 33/30* | (2006.01) |
| *A61K 33/34* | (2006.01) |
| *A61P 1/00* | (2006.01) |
| *A61P 1/14* | (2006.01) |

(52) U.S. Cl.
CPC .................. *A61K 33/38* (2013.01); *A61K 33/06* (2013.01); *A61K 33/24* (2013.01); *A61K 33/30* (2013.01); *A61K 33/34* (2013.01); *A61K 33/44* (2013.01)

(58) Field of Classification Search
CPC ... A61K 2300/00; A61K 33/38; A61K 33/06; A61K 33/24; A61K 33/30; A61K 33/34; A61K 33/44

See application file for complete search history.

(56) References Cited

U.S. PATENT DOCUMENTS

| | | | | |
|---|---|---|---|---|
| 4,366,085 | A  * | 12/1982 | Ikegami et al. | ............... 502/155 |
| 6,165,482 | A  * | 12/2000 | Grimberg | ...................... 424/405 |
| 7,687,433 | B2 | 3/2010 | Ko | |
| 2007/0122463 | A1 | 5/2007 | Ko | |
| 2008/0220162 | A1* | 9/2008 | Ko et al. | ....................... 427/215 |

OTHER PUBLICATIONS

Amin et al., Int. J. Mol. Sci., 2012, 13, 9923-9941.*
The Free Dictionary, obtained online at: http://www.thefreedictionary.com/solubility, downloaded on Apr. 7, 2015.*
The Free Dictionary, obtained online at: http://www.thefreedictionary.com/precipitate, downloaded on Apr. 7, 2015.*

* cited by examiner

*Primary Examiner* — Abigail Fisher
(74) *Attorney, Agent, or Firm* — Rabin & Berdo, P.C.

(57) ABSTRACT

A method of treating or preventing *Helicobacter pylori* infection in a subject, includes the step of orally administering to the subject a composition including a carbonaceous material that has a pore defined therein which has a radius of more than 0 nm but less than 2.5 nm; and from 0.001-15% by weight, based on weight of the carbonaceous material, of an active particle coated that is on the carbonaceous material and that is made of a material selected from the group consisting of silver, gold, aluminum, zinc, copper, and titanium dioxide.

18 Claims, 3 Drawing Sheets

PHARMACEUTICAL USE OF A COMPOSITION INCLUDING A CARBONACEOUS MATERIAL AND AN ACTIVE PARTICLE

CROSS REFERENCE TO RELATED APPLICATION(S)

The non-provisional application claims priority of Taiwan Patent Application NO. 102120013, filed on Jun. 5, 2013, the content thereof is incorporated by reference herein.

BACKGROUND OF THE INVENTION

1. Field of the Invention

The invention is directed to pharmaceutical use of a composition including a carbonaceous material and an active particle, and in particular, to a method of treating or preventing *Helicobacter pylori* infection in a subject by administering the composition to the subject.

2. Background of the Related Art

*Helicobacter pylori* is a Gram-negative microaerobic bacterium, and mainly lives in each region of the human stomach or duodenum. Since R. Warren and B. Marshall isolated *Helicobacter pylori* from a patient's stomach in 1982, many literatures have reported that *Helicobacter pylori* infection results in an attack of enterogastritis, and further causes an attack of gastric ulcers, duodenal ulcers, gastric lymphoma, or stomach cancer. The World Health Organization (WHO) proclaimed *Helicobacter pylori* was a Group 1 carcinogen for stomach cancer in 1994.

Presently, clinical treatment of *Helicobacter pylori* infection is a 3-in-1 treatment. In the 3-in-1 treatment, a patient concerned takes two antibiotics, e.g. Clarithromycin, Amoxicillin, Tetracycline, or Metronidazole, and one gastric acid-secretion inhibitor, e.g. Omeprazole or Lansoprazole. The antibiotics taking process needs to last for one week, and may last for two weeks if necessary; the gastric acid-secretion inhibitor taking process needs to last for two months, and may last for four months if necessary. However, during the whole treatment, side effects caused by such pharmaceuticals, e.g. dizziness, bitter taste in mouth, tongue coating, abdominal distention, loss of food taste, nausea, and diarrhea may be expected to the subject treated. The treatment is also considerably time-consuming for the patient. These lead to disobedience of the patient to the treatment, and thus are unfavorable to the cure of the infection. In another aspect, after the patient takes the antibiotics for a long term, *Helicobacter pylori* may be resistant to the antibiotics, resulting in un-favoring the drug selection for the future treatment of the infection or other diseases, as well as the cure of the infection.

In short, present pharmaceuticals for the treatment of *Helicobacter pylori* infection suffer from certain problems, such as side effects on a patient concerned and resistance to *Helicobacter pylori*. Accordingly, there is a need to provide a novel pharmaceutical for the treatment or prevention of *Helicobacter pylori* infection.

An object of the invention is to provide a novel pharmaceutical for the treatment or prevention of *Helicobacter pylori* infection.

SUMMARY OF THE INVENTION

For the and/or other object(s), the invention is to disclose a method of treating or preventing *Helicobacter pylori* infection in a subject. The method comprises the step(s) of: administering to the subject a composition including a carbonaceous material and an active particle. The active particle is coated on the carbonaceous material and made of a material selected from the group consisting of silver, gold, aluminum, zinc, copper, and titanium dioxide.

DETAILED DESCRIPTION OF THE INVENTION

The inventor disclosed an antimicrobial composition in US Patent Publication NO. 2007/0122463, and also pointed out that it could actively kill microbes. The inventor merely exemplified use of the composition for the treatment of skin injury. In another aspect, an activated carbon of the antimicrobial composition can absorb a toxicant in the stomach of a patient suffering from toxic poisoning, thereby having been in use of gastric lavage for the patient; a silver particle of the antimicrobial composition has been legitimately employed as an additive of the No. E174 food dye in European Union. That is, both of an activated carbon and a silver particle are edible in our daily life. The inventor believes that if a composition having an activated carbon and a silver particle associated with each other can kill *Helicobacter pylori*, such composition may then be in use of the treatment or prevention of *Helicobacter pylori* infection. The inventor also believes such composition is free from problems of side effects on a subject to whom it is administered and resistance on *Helicobacter pylori* due to the edible ingredients of the composition.

The invention is based on a discovery, in which an activated carbon fiber coated with a silver particle can effectively kill *Helicobacter pylori*. According to the discovery, the invention provides a method of treating or preventing *Helicobacter pylori* infection in a subject. The method comprises the steps of: administering to the subject a composition including a carbonaceous material and an active particle. The active particle is coated on the carbonaceous material and made of a material selected from the group consisting of silver, gold, aluminum, zinc, copper, and titanium dioxide. The term "treating" and derivatives thereof in the content indicate administering the composition to a subject suffered from *Helicobacter pylori* infection with the purpose to diminish, retard, or stop the increase or spread of infection, to diminish infection, or to cure infection. The term "preventing" and derivatives thereof in the content indicate administering the composition to a subject not suffered from *Helicobacter pylori* infection with the purpose to avoid infection, or to diminish or retard the increase or spread of infection.

Preferably, the composition is orally administered to the subject. The composition can be in the form of a food product for easy swallowing or drinking by the subject, such as, but not limited to, a health food or a health drink. As well, the composition can be in the form of a pharmaceutical for being taken by the subject, such as, but not limited to, a capsule, a tablet, a powder, a suspension, or an emulsifier.

Figure 1:
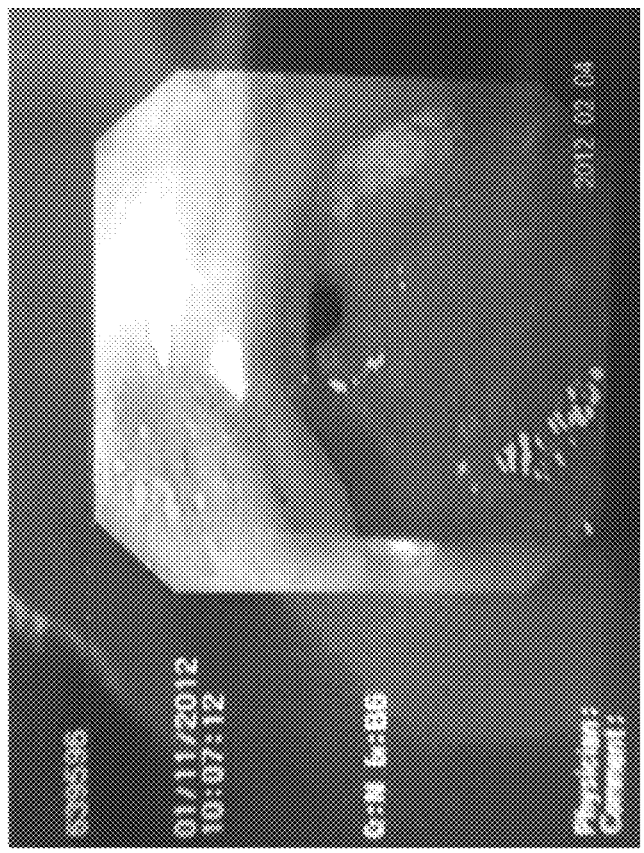
FIG. 1 is a gastroscopy picture illustrating the cure condition of a patient suffered from gastric ulcers caused by *Helicobacter pylori* infection on the 7th day after administration of the invention's composition to the patient.

As the following examples described, the carbonaceous material absorbs *Helicobacter pylori*, and then the active particle kills absorbed/unabsorbed *Helicobacter pylori*. In such a way, the composition can effectively eliminate *Helicobacter pylori* and be in use of the treatment or prevention of *Helicobacter pylori* infection. As shown in FIG. 1, a gastric disease caused by *Helicobacter pylori* infection in the subject, such as enterogastritis, gastric ulcers, or duodenal ulcers, is still able to be treated by administering the composition thereto.

An experiment taken in the laboratory indicates that on the 30th day after a laboratory rat taking the composition, there is no remaining of the active particle in the rat's liver, kidney, and blood, but a trace of the active particle found in the rat's excrements. This demonstrates that the active particle of the composition does not remain in the body of the subject so experimented.

The carbonaceous material of the composition is not limited to any specified one, as long as it can absorb *Helicobacter pylori*. An example of the carbonaceous material is, but not limited to, an activated carbon fiber, an activated carbon powder, a charcoal material, a bamboo charcoal granule, a carbon black, a graphite powder, a swelling graphite powder, or a carbon powder made from phenol formaldehyde resins or artificial resins. The surface area of the carbonaceous material is preferably of 400-2,500 $m^2/g$. The size of the active particle of the composition is not limited to any one, as long as the active particle can kill *Helicobacter pylori*. The particle diameter of the active particle is preferably of 1 nm-500 µm, and more preferably, of 5 nm-10 µm.

For improving absorption of *Helicobacter pylori* by the carbonaceous material, the carbonaceous material further has a pore thereon. Generally, the carbonaceous material still absorbs other material or probiotics in the subject, apart from *Helicobacter pylori*. To avoid such circumstance from occurring, the radius of the pore is preferably of more than 0 nm and less than 2.5 nm, and more preferably, of 0.5-2.3 nm.

For facilitating the composition to be orally administered to the subject, while the carbonaceous material is an activated carbon fiber, this material has following characteristics: a length of more than 0 mm and less than 0.1 mm, and a diameter of more than 0 µm and less than 10 µm.

For avoiding the active particle from coming off the carbonaceous material to cause damage to the subject, the amount of the active particle is preferably 0.001-15% by weight based on the weight of the carbonaceous material, and the leachability of the active particle in water is preferably more than 0 ppm and less than 100 ppm.

It is noted that the composition can be made via an impregnating method, a spraying method, or an electroplating method to coat the active particle on the carbonaceous material, or via the method in U.S. Pat. No. 7,687,433. While the carbonaceous material is an activated carbon fiber, a polyacrylonitrile (PAN) fiber, a pitch fiber, a phenol formaldehyde fiber, a lignin fiber, or a Rayon fiber is used as its starting material. After which, the starting material is converted to the activated carbon fiber by a process well known in the art. The detailed description of the process for producing the composition will be set forth in the following examples.

The following examples are offered to further illustrate the invention.

Example 1

A textile of a PAN fiber is prepared, and the textile has characteristics of: a fabric weight of 70 $g/m^2$, a pick count of 16 pick/inch, a BET surface area of 1,630 $m^2/g$, a density of 2.09 $g/m^3$, a carbon content of 85 wt %, and a silver content of 0 wt %.

In vacuum, the textile is dipped in a silver nitrite solution of 0.1 M (pH3.8) for 5 hours so as to reduce the silver ion to a silver block coated on the textile. Then, the textile coated with the silver block is dried to remove remaining water therein.

The dried textile is positioned in an oven full of nitrogen gas at a temperature of 400° C. for 90 minutes such that the silver block is split to a silver particle coated on the textile.

Figure 2:
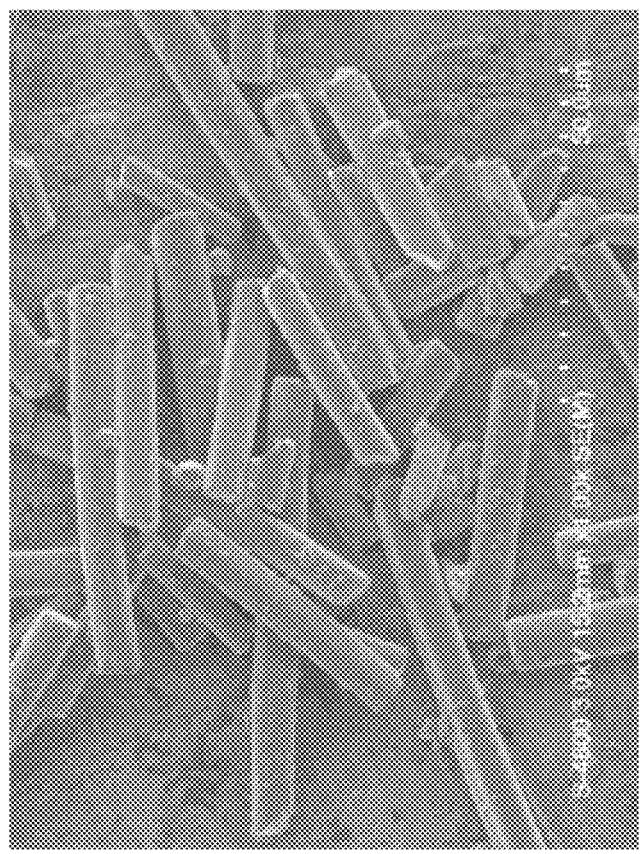
FIG. 2 is a scanning electron microscopy picture (×5,000) illustrating the appearance of a composition in Example 1.

The textile coated with the silver particle is grounded and sieved to generate an activated carbon fiber coated with a silver particle (FIG. 2). The combination of the activated carbon fiber and the silver particle is called composition hereafter.

The composition in this example possesses the following characteristics: a BET surface area of 1,200 $m^2/g$, a density of 2.13 $g/m^3$, a carbon content of 64 wt %, and a silver content of 12.5 wt %. The activated carbon fiber of the composition has the following characteristics: a length of 0.1 mm, a diameter of 6.0 µm, and a pore diameter of 2.41 nm. The silver particle of the composition has the following characteristics: a leachability in water of 15.75 ppm.

Example 2

In vacuum, a textile as that prepared in Example 1 is dipped in a silver nitrite solution of 0.1 M (pH3.8) for 5 hours, and then the silver ion is reduced to a silver block coated on the textile. The textile coated with the silver block is dried to remove remaining water therein.

The dried textile is positioned in a high temperature oven full of nitrogen gas at a temperature of 400° C. for 90 minutes such that the silver block is split to a silver particle coated on the textile.

The textile coated with the silver particle is washed with water at a speed of 4.5 l/min for 120 hours to remove uncoated silver particle. The washed textile is dried.

The dried textile is grounded and sieved to generate an activated carbon fiber coated with the silver particle. The combination of the activated carbon fiber and the silver particle is called as a composition hereafter.

The composition in this example possesses the following characteristics: a BET surface area of 1,220 $m^2/g$, a density of 2.13 $g/m^3$, and a silver content of 0.03 wt %. The activated carbon fiber of the composition has the following characteristics: a length of 0.1 mm, a diameter of 6.0 µm, and a pore diameter of 2.41 nm. The silver particle of the composition has the following characteristics: a leachability in water of 10.04 ppm.

Example 3

A felt of a phenol formaldehyde fiber is prepared, which has following characteristics: a fabric weight of 100 $g/m^2$, a BET surface area of 1,420 $m^2/g$, a density of 2.032 $g/m^3$, a carbon content of 85 wt %, and a silver content of 0 wt %.

In vacuum, the felt is dipped in a silver nitrite solution of 0.001 M (pH6.4) for 5 hours so that the silver ion is reduced to a silver block coated on the felt. Thereafter, the felt coated with the silver block is dried to remove remaining water therein.

The dried felt is placed in a high temperature oven full of nitrogen gas at a temperature of 400° C. for 90 minutes to split the silver block into a silver particle coated on the felt.

The felt coated with the silver particle is grounded and sieved to generate an activated carbon fiber coated with the silver particle. The combination of the activated carbon fiber and the silver particle is called composition hereafter.

The composition in this example possesses the following characteristics: a BET surface area of 1,380 m²/g, a density of 2.0425 g/m³, a carbon content of 75 wt %, and a silver content of 0.072 wt %. The activated carbon fiber of the composition has the following characteristics: a length of 0.1 mm, a diameter of 6.0 μm, and a pore diameter of 2.23 nm. The silver particle of the composition has the following characteristics: a leachability in water of 13.52 ppm.

Example 4

In vacuum, an activated carbon grain made from a plant is dipped in a silver nitrite solution of 0.008M and mixed with the solution by rotation at a speed of 50 rpm for 2 hours, and thus the silver ion is reduced to a silver block coated on the grain. The grain coated with the silver block is dried to remove remaining water therein.

Under an atmosphere full of nitrogen gas, the dried grain is heated to 600° C. at a ramp of 4° C./min, then stays at the temperature for 60 minutes, and finally is cooled to room temperature at a ramp of 10° C./min, so that the silver block is split to a silver particle coated on the grain.

After being washed with water, the grain coated with the silver particle is dried at a temperature of 120° C.

The dried grain is ground and sieved to generate an activated carbon powder coated with the silver particle. The combination of the activated carbon powder and the silver particle is called as a composition hereafter.

The composition in the example possesses the following characteristics: a BET surface area of 1,024 m²/g, a carbon content of 73.54 wt %, and a silver content of 0.22 wt %. The activated carbon powder of the composition has the following characteristics: a diameter of less than 0.1 mm and a pore diameter of 2.48 nm. The silver particle of the composition has the following characteristics: a particle diameter of 100-300 nm and a leachability in water of 30.49 ppm.

Comparative Example 1

A textile as used in Example 1 is grounded and sieved to obtain an activated carbon fiber with a length of 0.1 mm.

Comparative Example 2

A felt of a PAN fiber is grounded and sieved to obtain an activated carbon fiber with a length of 0.1 mm, and the felt has following characteristics: a fabric weight of 100 g/m², a BET surface area of 600 m²/g, a pore diameter of 2.07 nm, a density of 1.932 g/m³, a carbon content of 86 wt %, and a silver content of 0 wt %.

Comparative Example 3

A grain as that used in Example 4 is grounded and sieved to obtain an activated carbon powder having following characteristics: a diameter of less than 0.1 mm, a BET surface area of 1,135 m²/g, a carbon content of 84.24 wt %, and a pore diameter of 2.49 nm.

Analysis

Please refer to TABLE 1. The sterilization effect on different microbial species of the compositions in Examples 1-4, the activated carbon fibers in Comparative example 1-2, and the activated carbon powder in Comparative example 3 is listed in the table. The sterilization effect is expressed as a sterilizing rate which is measured according to the test method, ATCC (American Association of Textile Chemists and Colorists) 100-1998.

TABLE 1

Sterilization effect on different microbial species of the compositions in Examples 1-4, the activated carbon fibers in Comparative examples 1-2, and the activated carbon powder in Comparative example 3
Sterilizing rate

| | E. coli | P. aeruginosa | S. aureus | H. pylori | K. pneumonia |
|---|---|---|---|---|---|
| Example 1 | >99.98% | >99.98% | >99.98% | 94.12% | >99.99% |
| Example 2 | >99.98% | >99.98% | >99.98% | 93.05% | >99.99% |
| Example 3 | >99.98% | >99.98% | >99.98% | 94.06% | >99.99% |
| Example 4 | >99.98% | >99.98% | >99.98% | 90.68% | >99.98% |
| Comparative example 1 | 70.87% | 99.02% | 99.3% | 32.69% | <0% |
| Comparative example 2 | 20.31% | 33.52% | 58.1% | <0% | <0% |
| Comparative example 3 | 30.15% | 25.32% | 22.58% | <0% | <0% |

Though the activated carbon fiber in Example 1 is the same as that in Comparative example 1, the composition in Example 1 has a better sterilization effect on *Escherichia coli*, *Helicobacter pylori*, *Staphylococcus aureus*, and *Klebsiella pneumonia* than the activated carbon fiber in Comparative example 1.

The activated carbon powder in Example 4 is the same as that in Comparative example 3, but the composition in Example 4 has greater sterilization effect on *Escherichia coli*, *Pseudomonas aeruginosa*, *Helicobacter pylori*, *Staphylococcus aureus*, and *Klebsiella pneumonia* than the activated carbon powder in Comparative example 3.

Figure 3:
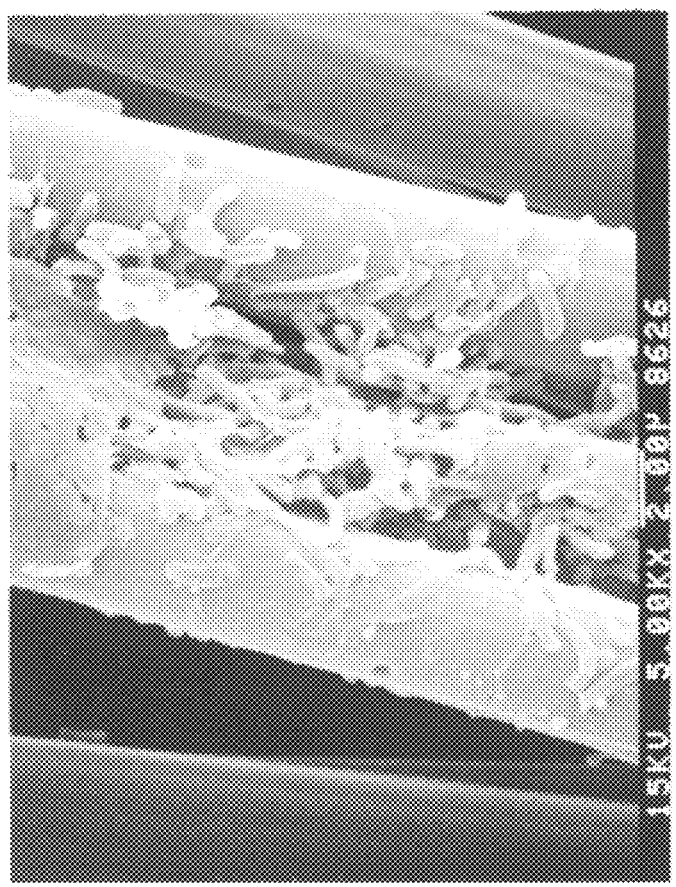
FIG. 3 is a scanning electron microscopy picture (×5,000) illustrating that a composition in Example 3 can absorb *Helicobacter pylori*.

Referring to FIG. 3, the figure shows the activated carbon fiber of the composition in Example 3 can absorb *Helicobacter pylori*. In addition, the silver particle thereof can release silver ion, particularly in water. As such, the silver ion can bind to a thiol group (—SH) of enzymes in absorbed/unabsorbed *Helicobacter pylori*, and effectively inhibit *Helicobacter pylori* due to the inactivation of these enzymes.

As above, it is approved that the composition of the invention can inhibit *Helicobacter pylori* and has a potential in use of the treatment or prevention of *Helicobacter pylori* infection. In another aspect, the carbonaceous material and the active particle of the composition are edible. While the composition is administered to a subject in need of the treatment or prevention, the composition has no side effects on the subject and resistance to *Helicobacter pylori*.

While the invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method of treating or preventing *Helicobacter pylori* infection in a subject, comprising the step of:
   orally administering to the subject a composition that is ingestible by the subject with substantially no side effects and consists of:
      a carbonaceous material that has pores defined therein, each pore of which has a radius of more than 0 nm but less than 2.5 nm, and that is effective to absorb *Helicobacter pylori*; and
      from 0.001-15% by weight, based on weight of the carbonaceous material, of active particles that are coated on the carbonaceous material, that are effective to kill *Helicobacter pylori*, and that are made of a material selected from the group consisting of silver, gold, aluminum, zinc, copper, and titanium dioxide.

2. The method as claimed in claim 1, wherein the carbonaceous material is selected from the group consisting of an activated carbon fiber, an activated carbon powder, a charcoal material, a bamboo charcoal granule, a carbon black, a graphite powder, a swelling graphite powder, and a carbon powder made from phenol formaldehyde resins or artificial resins.

3. The method as claimed in claim 2, wherein the carbonaceous material is an activated carbon fiber.

4. The method as claimed in claim 1, wherein the carbonaceous material has a surface area of 400-2,500 $m^2/g$.

5. The method as claimed in claim 1, wherein the active particles have a particle diameter of 1 nm-500 μm.

6. The method as claimed in claim 1, wherein the active particles have a leachability from the carbonaceous material in vivo that is less than that which could cause damage to the subject.

7. The method as claimed in claim 1, wherein the composition has a form of a capsule, a tablet, or a powder, or is included in a suspension or an emulsifier.

8. The method as claimed in claim 1, wherein the composition is included in a health food or a health drink.

9. The method as claimed in claim 1, wherein the method treats a gastric disease caused by a *Helicobacter pylori* infection in the subject, and wherein the disease is selected from the group consisting of enterogastritis, gastric ulcers, and duodenal ulcers.

10. The method as claimed in claim 1, wherein the composition is ingestible by the subject with no side effects.

11. The method as claimed in claim 3, wherein the carbonaceous material has a length of more than 0 mm and less than 0.1 mm, and a diameter of more than 0 μm and less than 10 μm.

12. The method as claimed in claim 3, wherein the material of the active particles is silver.

13. The method as claimed in claim 12, wherein the carbonaceous material has a length of more than 0 mm and less than 0.1 mm, and a diameter of more than 0 μm and less than 10 μm.

14. The method as claimed in claim 12, wherein the active particles have a particle diameter of 1 nm-500 μm.

15. The method as claimed in claim 12, wherein the active particles have a leachability from the carbonaceous material in vivo that is less than that which could cause damage to the subject.

16. The method as claimed in claim 12, wherein the composition has a form of a capsule, a tablet, or a powder, or is included in a suspension or an emulsifier.

17. The method as claimed in claim 12, wherein the composition is included in a health food or a health drink.

18. The method as claimed in claim 12, wherein the method treats a gastric disease caused by a *Helicobacter pylori* infection in the subject, and wherein the disease is selected from the group consisting of enterogastritis, gastric ulcers, and duodenal ulcers.

\* \* \* \* \*